US011788023B2

(12) United States Patent
Womeldorff et al.

(10) Patent No.: US 11,788,023 B2
(45) Date of Patent: *Oct. 17, 2023

(54) SYSTEMS AND METHODS OF CONVERTING RENEWABLE FEEDSTOCKS INTO INTERMEDIATE HYDROCARBON BLEND STOCKS AND TRANSPORTATION FUELS

(71) Applicant: MARATHON PETROLEUM COMPANY LP, Findlay, OH (US)

(72) Inventors: Justin L. Womeldorff, Findlay, OH (US); Jeffrey A. Sexton, Findlay, OH (US); David Linington, Findlay, OH (US)

(73) Assignee: MARATHON PETROLEUM COMPANY LP, Findlay, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/112,565

(22) Filed: Feb. 22, 2023

(65) Prior Publication Data
US 2023/0203390 A1 Jun. 29, 2023

Related U.S. Application Data

(63) Continuation of application No. 17/848,443, filed on Jun. 24, 2022, now Pat. No. 11,613,715.

(60) Provisional application No. 63/262,426, filed on Oct. 12, 2021.

(51) Int. Cl.
C10L 1/02 (2006.01)
C10L 1/06 (2006.01)
C12P 7/06 (2006.01)
C10L 1/14 (2006.01)

(52) U.S. Cl.
CPC ....... *C10L 1/146* (2013.01); *C10L 2200/0484* (2013.01); *C10L 2270/026* (2013.01); *C10L 2290/24* (2013.01); *C10L 2300/20* (2013.01)

(58) Field of Classification Search
CPC ............. C10L 1/146; C10L 2200/0484; C10L 2270/026; C10L 2290/24; C10L 2300/20
See application file for complete search history.

(56) References Cited

U.S. PATENT DOCUMENTS

| | | | |
|---|---|---|---|
| 4,904,383 A | 2/1990 | Auerswald | |
| 7,244,364 B1 | 7/2007 | Weber | |
| 7,872,054 B2 | 1/2011 | Cortright et al. | |
| 7,989,664 B2 | 8/2011 | Cortright | |
| 8,017,818 B2 | 9/2011 | Cortright et al. | |
| 8,192,628 B2 | 6/2012 | Cranford et al. | |
| 8,231,857 B2 | 7/2012 | Cortright et al. | |
| 8,273,138 B2 | 9/2012 | Bauldreay et al. | |
| 8,350,108 B2 | 1/2013 | Cortright et al. | |
| 8,466,330 B2 | 6/2013 | Bauldreay et al. | |
| 8,642,813 B2 | 2/2014 | Qiao et al. | |
| 8,697,924 B2 | 4/2014 | Bauldreay et al. | |
| 8,710,281 B2 | 4/2014 | Nagaki et al. | |
| 8,784,645 B2 | 7/2014 | Iguchi et al. | |
| 8,834,587 B2 | 9/2014 | Cortright et al. | |
| 8,962,902 B2 | 2/2015 | Blommel et al. | |
| 9,206,366 B2 | 12/2015 | Bauldreay et al. | |
| 9,314,778 B2 | 4/2016 | Blank et al. | |
| 9,453,169 B2 | 9/2016 | Stippich, Jr. et al. | |
| 9,593,054 B2 | 3/2017 | Kania et al. | |
| 9,656,937 B2 | 5/2017 | Held et al. | |
| 9,725,777 B2 | 8/2017 | Qiao et al. | |
| 9,765,261 B2 | 9/2017 | Qiao et al. | |
| 9,862,893 B2 | 1/2018 | Gray et al. | |
| 9,873,836 B2 | 1/2018 | Blommel et al. | |
| 9,873,837 B2 | 1/2018 | Qiao et al. | |
| 9,878,966 B2 | 1/2018 | Blommel et al. | |

(Continued)

FOREIGN PATENT DOCUMENTS

| | | |
|---|---|---|
| CN | 103627433 | 3/2014 |
| WO | 2006/005085 | 1/2006 |
| WO | 2014/066396 | 5/2014 |

OTHER PUBLICATIONS

Van Dyk et al., "Potential synergies of drop-in biofuel production with further co-processing at oil refineries", Biofuels, Bioproducts and Biorefining, Society of Chemical Industry and John Wiley & Sons, Ltd., pp. 760-775, 2019.

Pathak et al., (Chapter 9: Feedstock Transportation, Agricultural Processing, Logistic from Farm to Bio-refinery: Recent Developments, Mechanization, and Cost Analysis in Sustainable Biofuels Development in India, Chandal, Sukumaran, Springer, 2017, pp. 207-221). (Year: 2017).

Show et al., ("Algal biomass dehydration", Bioresource Technology, 2013, 135, 720-729). (Year: 2013).

Humooudi et al., (American Scientific research Journal for Engineering, Technology and Sciences, 2017, 36, 224-241). (Year: 2017).

(Continued)

Primary Examiner — Ellen M McAvoy
Assistant Examiner — Chantel Graham
(74) Attorney, Agent, or Firm — Womble Bond Dickinson (US) LLP

(57) ABSTRACT

Systems and methods to provide renewable transportation fuels for internal combustion engines by converting renewable feedstocks into two or more intermediate hydrocarbon blend stocks and blending at least two of the two or more intermediate hydrocarbon blend stocks to produce the renewable transportation fuel. Methods and/or processes may include selecting sugar from a sugar source and introducing the sugar into one or more reactors. The sugar may be converted into an intermediate renewable hydrocarbon blend stock and sent to a separation unit to separate out an intermediate renewable gasoline unit. The process may include selecting and converting a lipid from a lipid source into a renewable diesel product. The renewable diesel product may be sent to a second separation unit to separate out renewable diesel and a low-grade naphtha. The low-grade naphtha and intermediate renewable gasoline may be blended to define a finished renewable gasoline.

20 Claims, 8 Drawing Sheets

(56) References Cited

U.S. PATENT DOCUMENTS

| | | |
|---|---|---|
| 9,988,585 B2 | 6/2018 | Hayasaka et al. |
| 10,005,700 B2 | 6/2018 | Beck et al. |
| 10,071,322 B2 | 9/2018 | Coppola et al. |
| 10,370,596 B2 | 8/2019 | Blommel et al. |
| 10,975,319 B2 | 4/2021 | Price et al. |
| 11,130,914 B2 | 9/2021 | Blommel et al. |
| 11,306,260 B1 | 4/2022 | Cox |
| 11,352,570 B1 | 6/2022 | Cox |
| 11,702,601 B2 | 7/2023 | Cantley et al. |
| 11,725,151 B2 | 8/2023 | Cox |
| 2008/0149486 A1 | 6/2008 | Greaney et al. |
| 2009/0159426 A1 | 6/2009 | Chen |
| 2012/0280175 A1 | 11/2012 | Kania et al. |
| 2012/0323053 A1 | 12/2012 | Qiao et al. |
| 2013/0019859 A1 | 1/2013 | Qiao et al. |
| 2013/0023702 A1 | 1/2013 | Qiao et al. |
| 2013/0036660 A1* | 2/2013 | Woods ............ C10L 1/06 585/24 |
| 2013/0043192 A1 | 2/2013 | Smith et al. |
| 2014/0187828 A1* | 7/2014 | Bauldreay ............ C10G 3/45 585/14 |
| 2014/0350317 A1 | 11/2014 | Blommel et al. |
| 2015/0165488 A1 | 6/2015 | Powell et al. |
| 2015/0183701 A1 | 7/2015 | Blank et al. |
| 2015/0315055 A1 | 11/2015 | Chidambaran et al. |
| 2016/0115432 A1 | 4/2016 | Dahiya |
| 2016/0214028 A1 | 7/2016 | Coppola et al. |
| 2016/0326448 A1 | 11/2016 | Bauldreay et al. |
| 2016/0362756 A1 | 12/2016 | Qiao et al. |
| 2017/0044443 A1 | 2/2017 | Blommel et al. |
| 2020/0048569 A1* | 2/2020 | Karvo ............ C10L 1/06 |
| 2020/0172817 A1 | 6/2020 | Davidson et al. |
| 2021/0009911 A1* | 1/2021 | Medoff ............ C10G 3/47 |
| 2022/0041939 A1 | 2/2022 | Tiitta et al. |
| 2022/0135449 A1 | 5/2022 | Cantley et al. |
| 2023/0072588 A1 | 3/2023 | Blommel et al. |
| 2023/0122414 A1 | 4/2023 | Blommel et al. |
| 2023/0125062 A1 | 4/2023 | Blommel et al. |

OTHER PUBLICATIONS

Lavanya et al., (Bioresource Technology, 2016, 203, 228-235). (Year: 2016).

Pruneda et al., (J. Mex. Chem. Soc. 2005, 49, 14-19). (Year: 2005).

* cited by examiner

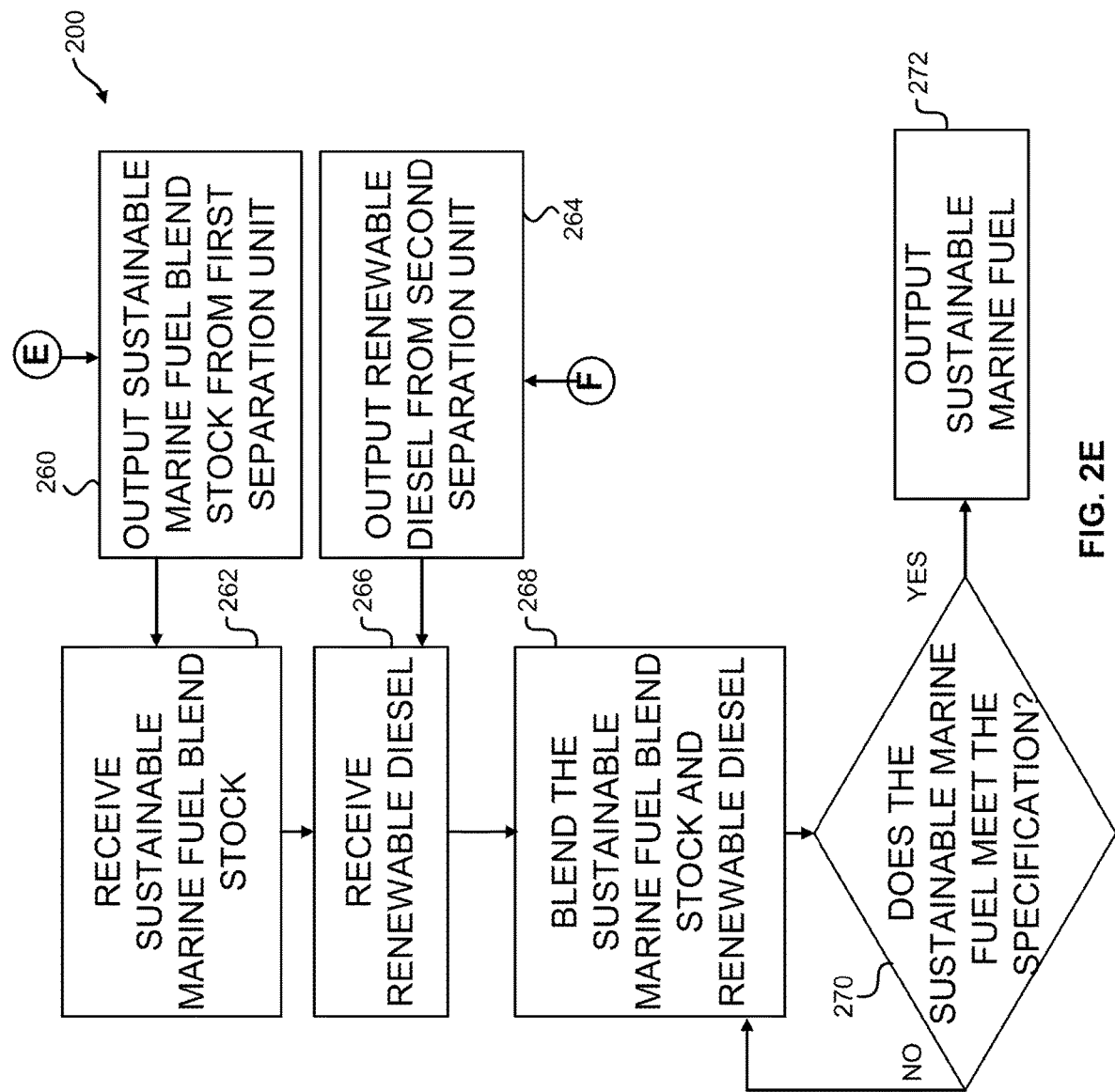

SYSTEMS AND METHODS OF CONVERTING RENEWABLE FEEDSTOCKS INTO INTERMEDIATE HYDROCARBON BLEND STOCKS AND TRANSPORTATION FUELS

PRIORITY CLAIM

This is a continuation of U.S. Non-Provisional application Ser. No. 17/848,443, filed Jun. 24, 2022, titled "SYSTEMS AND METHODS OF CONVERTING RENEWABLE FEEDSTOCKS INTO INTERMEDIATE HYDROCARBON BLEND STOCKS AND TRANSPORTATION FUELS," which claims priority to and the benefit of U.S. Provisional Application No. 63/262,426, filed Oct. 12, 2021, titled "SYSTEMS AND METHODS OF CONVERTING RENEWABLE FEEDSTOCKS INTO INTERMEDIATE HYDROCARBON BLEND STOCKS AND TRANSPORTATION FUELS," the disclosures of which are incorporated herein.

FIELD OF THE DISCLOSURE

Embodiments herein generally relate to renewable transportation fuels. More specifically, one or more embodiments relate to converting renewable feedstocks into two or more intermediate hydrocarbon blend stocks and blending at least two of the two or more intermediate hydrocarbon blend stocks to produce the renewable transportation fuel.

BACKGROUND

Technologies have been developed to produce refined products for use in transportation fuels using renewable feedstock or materials. These products may be transported to a traditional refinery or terminal to be blended into fossil-based fuels. The renewable diesel facilities, ethanol plants and/or other renewable transportation fuel units are typically located at separate sites or locations apart from each other and traditional refineries/terminals. As such, products produced by each facility must be transported for blending or further processing. For example, the diesel product formed by some renewable diesel facilities contain ringed components, have low cetane (e.g., a cetane number between about −30 to 10), and is dark in color. Such a diesel product cannot be blended into California Air Resources Board (CARB) diesel or ultra-low sulfur diesel (ULSD) diesel at appreciable volumes without further processing.

SUMMARY

Accordingly, Applicants have recognized a need for systems and methods to provide renewable transportation fuels for internal combustion engines by converting renewable feedstocks into two or more intermediate hydrocarbon blend stocks and blending at least two of the two or more intermediate hydrocarbon blend stocks to produce the renewable transportation fuel. The renewable feedstocks may be produced at a refinery or facility via co-located, on-site units. The integration of the co-located, on-site units enables a refinery or facility to fully utilize renewable feedstocks. The refinery or facility leverages co-location efficiencies, economies of scale associated with support infrastructure, and operating expense savings. Such systems and methods allow for the further processing of renewable feedstocks without the need for carbon-intensive and expensive transportation. The present disclosure is directed to embodiments of such systems and methods.

The present disclosure is generally directed to systems and methods for providing renewable transportation fuels for internal combustion engines by converting renewable feedstocks into two or more intermediate hydrocarbon blend stocks and blending at least two of the two or more intermediate hydrocarbon blend stocks to produce the renewable transportation fuel. The renewable feedstocks may be produced at a refinery or facility via co-located, on-site units. The conversion and separation of sugar from a source and lipids from a source may produce two or more renewable feedstocks. At least two of the two or more renewable feedstocks may be blended to produce a renewable transportation fuel. The renewable transportation fuel may include a renewable gasoline, renewable aviation fuel, renewable or sustainable marine fuel, or renewable liquefied petroleum gas (LPG). The integration of the co-located, on-site units enables the refinery or facility to utilize and produce fully renewable feedstocks by leveraging co-location efficiencies and existing support infrastructure.

Accordingly, an embodiment of the disclosure is directed to a process to provide renewable transportation fuels for internal combustion engines by converting renewable feedstocks into two or more intermediate hydrocarbon blend stocks and blending at least two of the two or more intermediate hydrocarbon blend stocks to produce the renewable transportation fuel. The process may include introducing sugar into one or more reactors. The process may include converting the sugar into an intermediate renewable hydrocarbon blend stock through hydrogenation of the sugar, hydrodeoxygenation of the hydrogenated sugar, and acid condensation of the hydrodeoxygenated, and hydrogenated sugar within the one or more reactors. The process may include passing the intermediate renewable hydrocarbon blend stock through a first separation unit to separate out at least an intermediate renewable gasoline blend stock. The process may include introducing one or more lipids into a renewable diesel unit. The process may include operating the renewable diesel unit to yield a renewable diesel product from the one or more lipids. The renewable diesel product may include at least a low-grade naphtha and a renewable diesel via a hydrotreated vegetable oil or hydroprocessed esters and fatty acids process. The process may include passing the renewable diesel product through a second separation unit to separate out at least a renewable diesel and a low-grade naphtha. The low-grade naphtha may have a benzene content less than about 0.5 volume percent and a research octane number of less than about 60. The process may include blending the low-grade naphtha and the intermediate renewable gasoline blend stock to define a finished renewable gasoline; and outputting the finished renewable gasoline for use in internal combustion engines.

In another embodiment, the process may further include introducing a carbohydrate feedstock to an ethanol plant. The process may include operating an ethanol fermentation and distillation process in the ethanol plant to convert the carbohydrate feedstock into at least an ethanol product. The process may include separating an ethanol blend stock from the ethanol product in an ethanol separator. The process may include blending the ethanol blend stock with the low-grade naphtha and the intermediate renewable gasoline blend stock to define the finished renewable gasoline.

In another embodiment, the process may include, prior to introducing the sugar to one or more reactors, selecting the sugar from a sugar source. The sugar source may be a wet or dry mill. The process may further include, prior to introducing the one or more lipids into the renewable diesel unit, selecting the one or more lipids from a lipid source. The one or more lipids may comprise one or more of vegetable oils, animal fats, used cooking oil, other lipids, or some combination thereof.

In another embodiment, the process may further include introducing renewable natural gas as a reformer unit feedstock to a reformer unit. The process may include producing at least hydrogen gas through conversion of the renewable natural gas in the reformer unit. The process may include introducing at least a portion of the hydrogen gas into at least one of the one or more reactors to hydrogenate the sugar or dehydrodeoxygenate the hydrogenated sugar.

In another embodiment, the process may further include introducing renewable natural gas as a reformer unit feedstock to a reformer unit. The process may include producing at least hydrogen gas by conversion of the renewable natural gas in the reformer unit. The process may include introducing at least a portion of the hydrogen gas into the renewable diesel unit to produce the renewable diesel and the low-grade naphtha.

In another embodiment, the intermediate renewable hydrocarbon blend stock further includes a first sustainable aviation fuel blend stock that contains synthesized kerosene (SK) or synthesized aromatic kerosene (SAK) and the renewable diesel product further includes a second sustainable aviation fuel blend stock that contains hydroprocessed esters and fatty acids-synthetic paraffinic kerosene (HEFA-SPK). In such embodiments, the process may further include separating the first sustainable aviation fuel blend stock from the intermediate renewable hydrocarbon blend stock in the first separation unit. The process may include separating the second sustainable aviation fuel blend stock from the renewable diesel unit in the second separation unit. The process may include blending the first sustainable aviation fuel blend stock and the second sustainable aviation fuel blend stock into a renewable sustainable aviation fuel.

In another embodiment, the intermediate renewable hydrocarbon blend stock may further include a precursor marine fuel blend stock. In such embodiments, the process may include separating the precursor marine fuel blend stock from the intermediate renewable hydrocarbon blend stock in the first separation unit. The process may include blending an amount of the renewable diesel with the precursor marine fuel blend stock to define a renewable marine fuel.

In another embodiment, the finished renewable gasoline may be output as a non-petroleum based fuel. The finished renewable gasoline may be substantially devoid of any fossil fuel-derived components.

Another embodiment of the disclosure is directed to a process to provide renewable transportation fuels for internal combustion engines by converting renewable feedstocks into two or more intermediate hydrocarbon blend stocks and blending at least two of the two or more intermediate hydrocarbon blend stocks to produce the renewable transportation fuel. The process may include introducing a sugar into one or more reactors. The process may include converting the sugar into an intermediate renewable hydrocarbon blend stock through hydrogenation of the sugar, hydrodeoxygenation of the hydrogenated sugar, and acid condensation of the hydrodeoxygenated, hydrogenated sugar within the one or more reactors. The process may include passing the intermediate renewable hydrocarbon blend stock through a first separation unit to separate out at least a first sustainable aviation fuel blend stock that contains synthesized kerosene (SK) or synthesized aromatic kerosene (SAK). The process may include introducing one or more lipids into a renewable diesel unit. The process may include operating the renewable diesel unit to yield a renewable diesel product from the one or more lipids. The process may include passing the renewable diesel product through a second separation unit to separate out at least a second sustainable aviation fuel blend stock that has at least one of hydroprocessed esters and fatty acids-synthetic paraffinic kerosene (HEFA-SPK). The process may include receiving the first sustainable aviation fuel blend stock from the first separation unit. The process may include receiving the second sustainable aviation fuel blend stock from the second separation unit. The process may include blending at least the first sustainable aviation fuel blend stock and the second sustainable aviation fuel blend stock to define a sustainable aviation fuel. The process may include outputting the sustainable aviation fuel for use in internal combustion engines.

Another embodiment of the disclosure is directed to a process to provide renewable transportation fuels for internal combustion engines by converting renewable feedstocks into two or more intermediate hydrocarbon blend stocks and blending at least two of the two or more intermediate hydrocarbon blend stocks to produce the renewable transportation fuel. The process may include selecting sugar from a sugar source. The process may include introducing the sugar into one or more reactors. The process may include converting the sugar into an intermediate renewable hydrocarbon blend stock through hydrogenation of the sugar, hydrodeoxygenation of the hydrogenated sugar, and acid condensation of the hydrodeoxygenated, hydrogenated sugar within the one or more reactors. The process may include passing the intermediate renewable hydrocarbon blend stock through a first separation unit to separate out at least a sustainable marine fuel blend stock. The process may include selecting one or more lipids from a lipid source. The process may include introducing the one or more lipids into a renewable diesel unit. The process may include operating the renewable diesel unit to yield a renewable diesel product from the one or more lipids. The process may include passing the renewable diesel product through a second separation unit to separate out at least a renewable diesel. The process may include receiving the sustainable marine fuel blend stock from the first separation unit. The process may include receiving the renewable diesel from the second separation unit. The process may include blending at least the sustainable marine fuel blend stock and the renewable diesel to define a sustainable marine fuel. The process may include outputting the sustainable marine fuel for use in internal combustion engines.

Another embodiment of the disclosure is directed to a process to provide renewable transportation fuels for internal combustion engines by converting renewable feedstocks into two or more intermediate hydrocarbon blend stocks and blending at least two of the two or more intermediate hydrocarbon blend stocks to produce the renewable transportation fuel. The process may include selecting sugar from a sugar source. The process may include introducing the sugar into one or more reactors. The process may include converting the sugar into an intermediate renewable hydrocarbon blend stock through hydrogenation of the sugar, hydrodeoxygenation of the hydrogenated sugar, and acid condensation of the hydrodeoxygenated, hydrogenated sugar within the one or more reactors. The process may include passing the intermediate renewable hydrocarbon blend stock through a first separation unit to separate out at least a first intermediate light ends stream containing first intermediate light ends. The process may include selecting one or more lipids from a lipid source. The process may include introducing the one or more lipids into a renewable diesel unit. The process may include operating the renewable diesel unit to yield a renewable diesel product from the one or more lipids. The process may include passing the renewable diesel product through a second separation unit to separate out at least a second intermediate light ends steam containing second intermediate light ends. The process may include introducing the first intermediate light ends from the first intermediate lights ends stream and the second intermediate light ends from the second intermediate light ends stream into a third separation unit. The process may include operating the third separation unit to separate the first and second intermediate lights ends into at least a renewable LPG product and a fuel gas. The process may include outputting the renewable LPG product for use in internal combustion engines.

In another embodiment, the process may include passing the fuel gas to a steam reformer. The process may include combusting at least a portion of the fuel gas to produce hydrogen gas in the steam reformer.

Accordingly, another embodiment of the disclosure is directed to a system to provide renewable transportation fuels for internal combustion engines that converts renewable feedstocks into two or more intermediate hydrocarbon blend stocks and blends at least two of the two or more intermediate hydrocarbon blend stocks to produce the renewable transportation fuel. The system may include a source of sugar. The system may include at least one reactor with an inlet to receive the sugar from the source of sugar and an outlet. The at least one reactor may be configured to hydrogenate the sugar, hydrodeoxygenate the hydrogenated sugar, and facilitate acid condensation of the hydrodeoxygenated, hydrogenated sugar to produce an intermediate renewable hydrocarbon blend stock. The system may include a first separation unit connected to and in fluid communication with the outlet of the at least one reactor. The first separation unit may be operable to separate the intermediate renewable hydrocarbon blend stock into at least an intermediate renewable gasoline blend stock. The system may include a source of lipids. The system may include a renewable diesel unit with an inlet to receive the lipid from the source of lipids and an outlet. The renewable diesel unit may be configured to yield a renewable diesel product from the one or more lipids. The system may include a second separation unit connected to and in fluid communication with the outlet of the renewable diesel unit. The second separation unit may be operable to separate the renewable diesel product into at least a renewable diesel blend stock and a low-grade naphtha. The low-grade naphtha may have a benzene content less than about 0.5 volume percent and a research octane number of less than about 60.

In another embodiment, the system may include a source of carbohydrate feedstock. The system may include an ethanol production plant with an inlet that receives the carbohydrate feedstock from the source of carbohydrate feedstock. The ethanol production plant may be operable to convert the carbohydrate feedstock into an ethanol blend stock that leaves the ethanol production plant through an outlet thereof. The system may include a flow line between the outlet of the ethanol production plant and the blending unit to pass the ethanol blend stock to the blending unit for blending with the intermediate renewable gasoline blend stock and the low-grade naphtha.

Accordingly, anther embodiment of the disclosure is directed to a method for producing renewable transportation fuels, within a refinery, for internal combustion engines that converts renewable feedstocks into two or more intermediate hydrocarbon blend stocks and blends at least two of the two or more intermediate hydrocarbon blend stocks to produce the renewable transportation fuel. The method may include introducing sugar to one or more reactors co-located with a refinery. The method may include converting the sugar into an intermediate renewable hydrocarbon blend stock through within the one or more reactors. The method may include separating the intermediate renewable hydrocarbon blend stock into a first intermediate renewable blend stock within a first separation unit co-located with the refinery. The method may include introducing one or more lipids into a renewable diesel unit co-located with the refinery. The method may include operating the renewable diesel unit to yield a renewable diesel product from the one or more lipids. The method may include separating the renewable diesel product into a second intermediate renewable blend stock within a second separation unit co-located with the refinery. The method may include blending the first intermediate blend stock and the second intermediate blend stock within a blend unit co-located with the refinery. A blend of the first intermediate blend stock and the second intermediate blend stock to define a finished renewable transportation fuel.

Still other aspects and advantages of these and other embodiments are discussed in detail herein. Moreover, it is to be understood that both the foregoing information and the following detailed description provide merely illustrative examples of various aspects and embodiments and are intended to provide an overview or framework for understanding the nature and character of the claimed aspects and embodiments. Accordingly, the advantages and features of the present disclosure will become more apparent through reference to the following description and the accompanying drawings. Furthermore, it is to be understood that the features of the various embodiments described herein are not mutually exclusive and may exist in various combinations and permutations.

BRIEF DESCRIPTION OF DRAWINGS

These and other features, aspects, and advantages of the disclosure will become better understood with regard to the following descriptions, claims, and accompanying drawings. It is to be noted, however, that the drawings illustrate only several embodiments of the disclosure and, therefore, are not to be considered limiting of the scope of the disclosure.

FIGS. 2A through 2F are flow diagrams for producing renewable transportation fuel at a co-located refinery, according to one or more embodiments disclosed herein.

DETAILED DESCRIPTION

Figure 1:
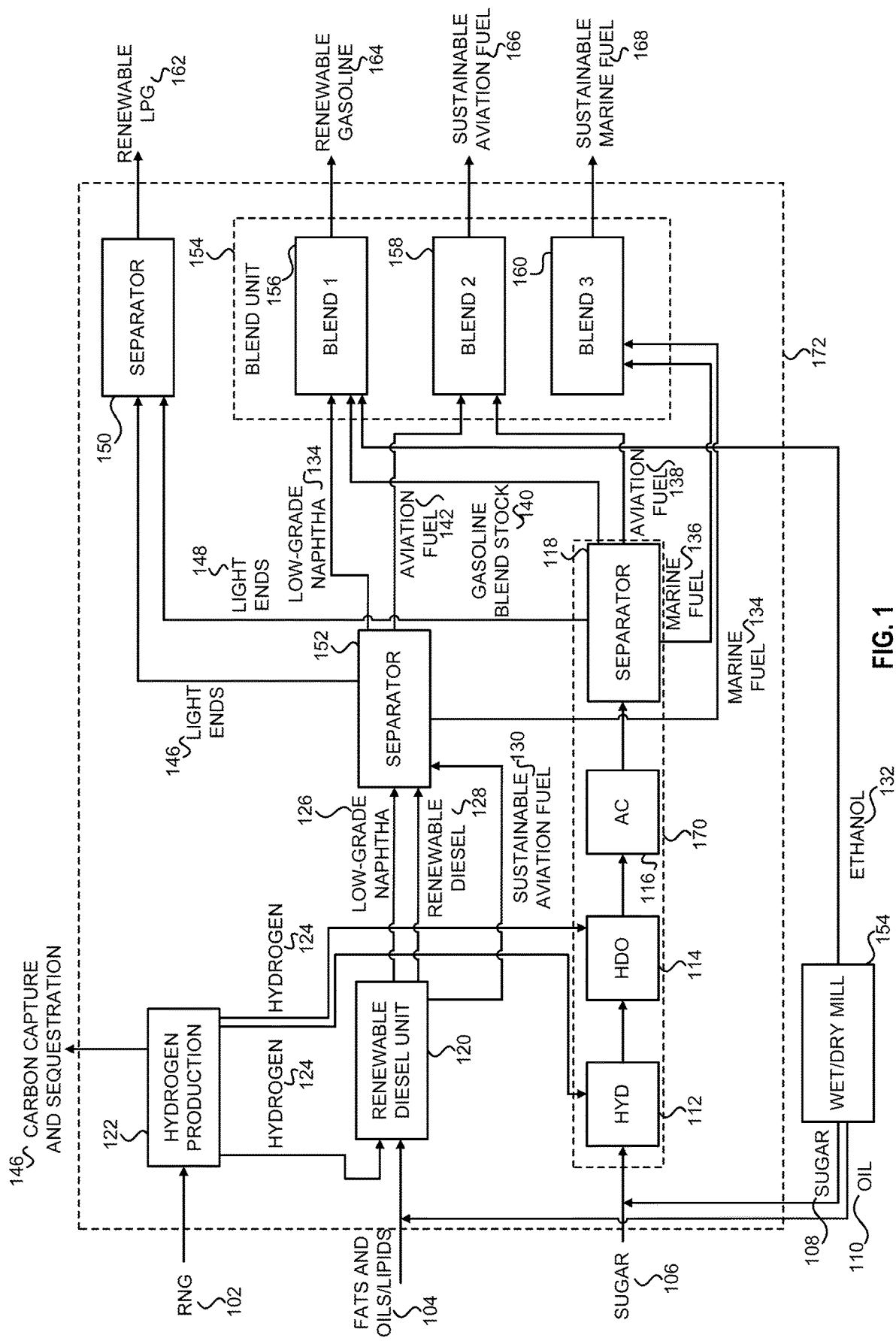
FIG. 1 is a schematic diagram of a co-located refinery, according to one or more embodiments disclosed herein.
Figure 2A:
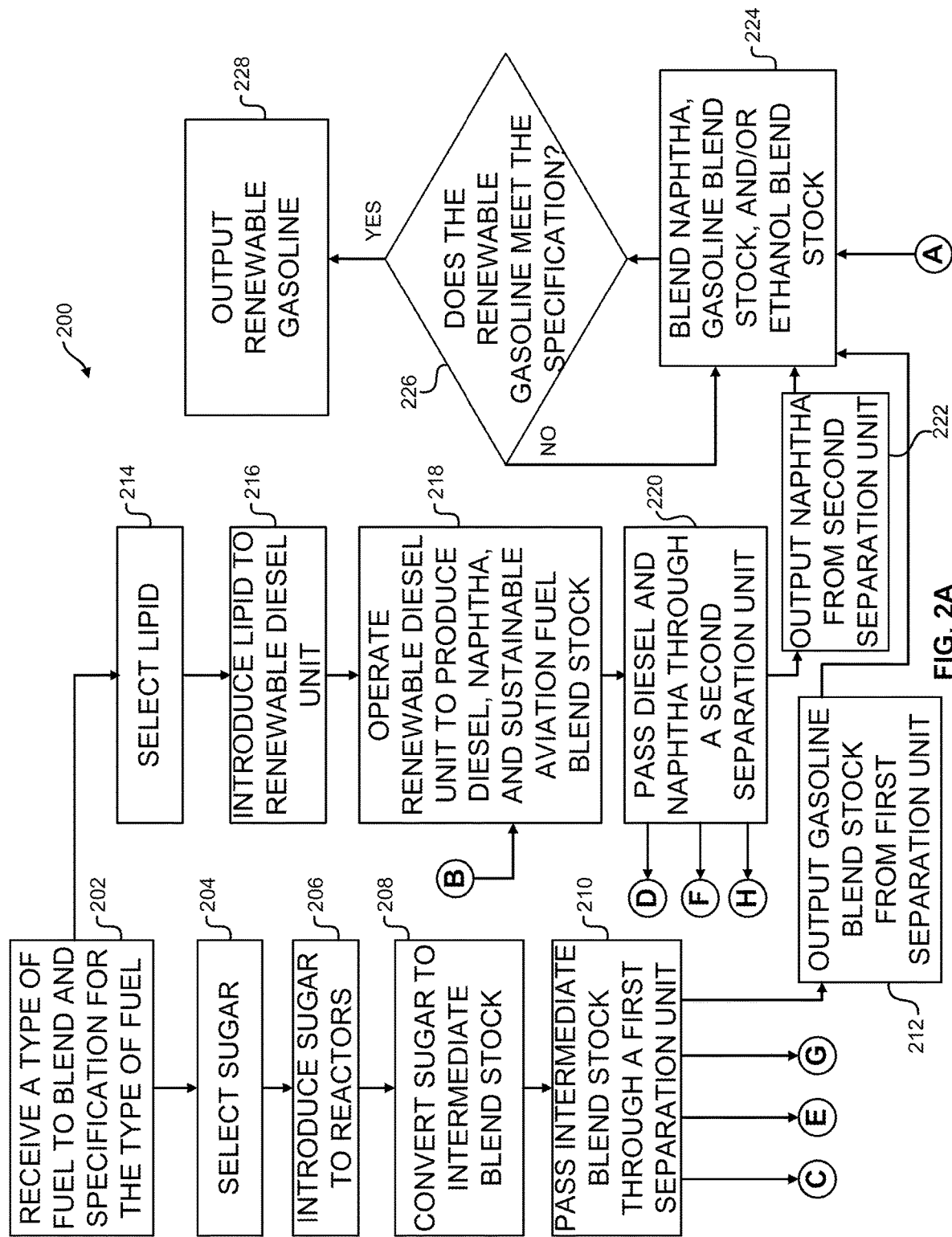
Figure 2C:
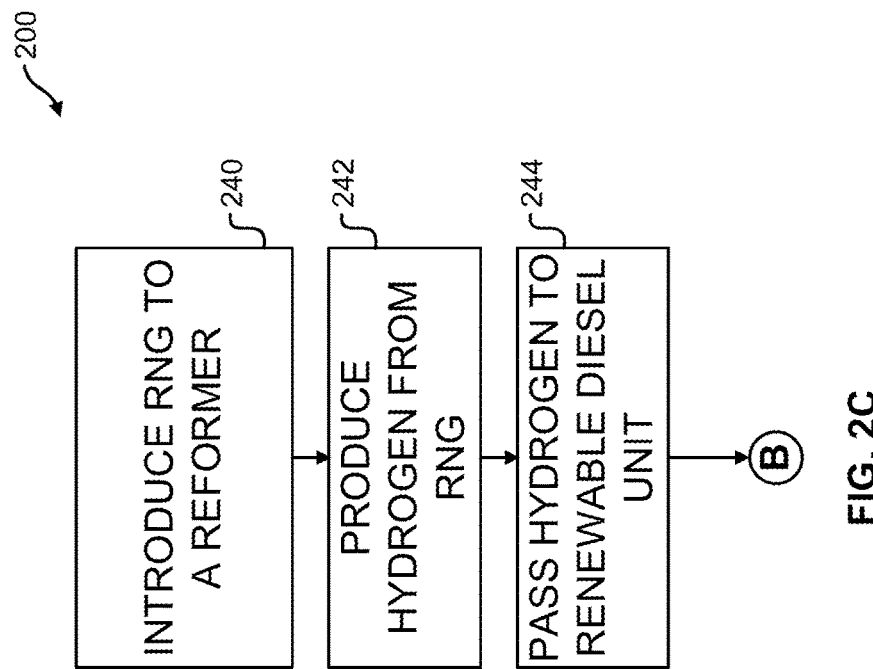
Figure 2B:
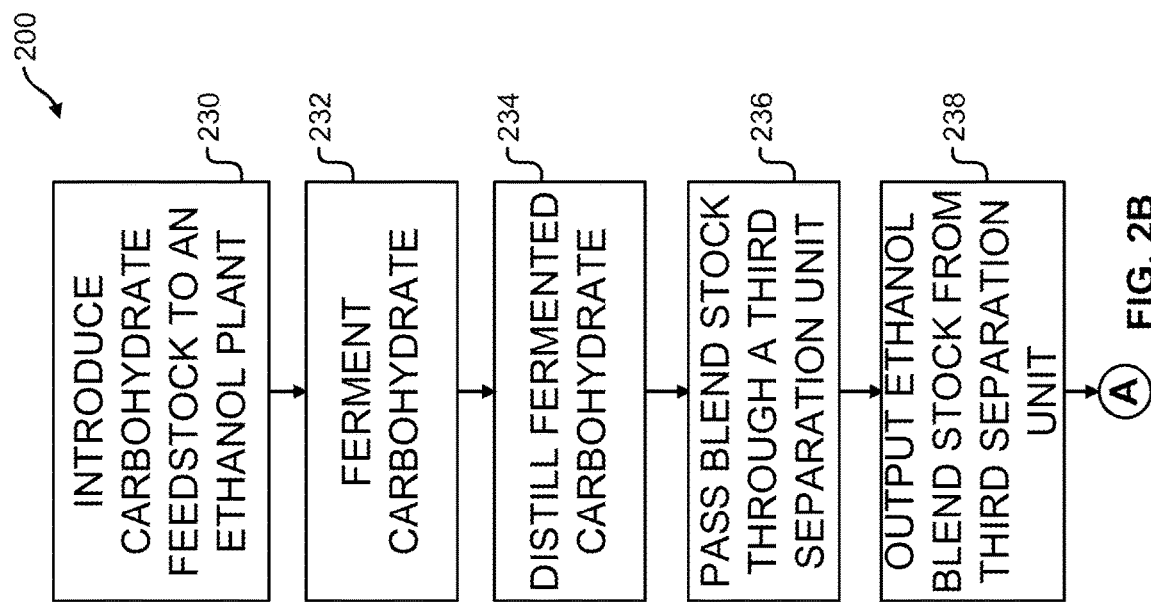
Figure 2D:
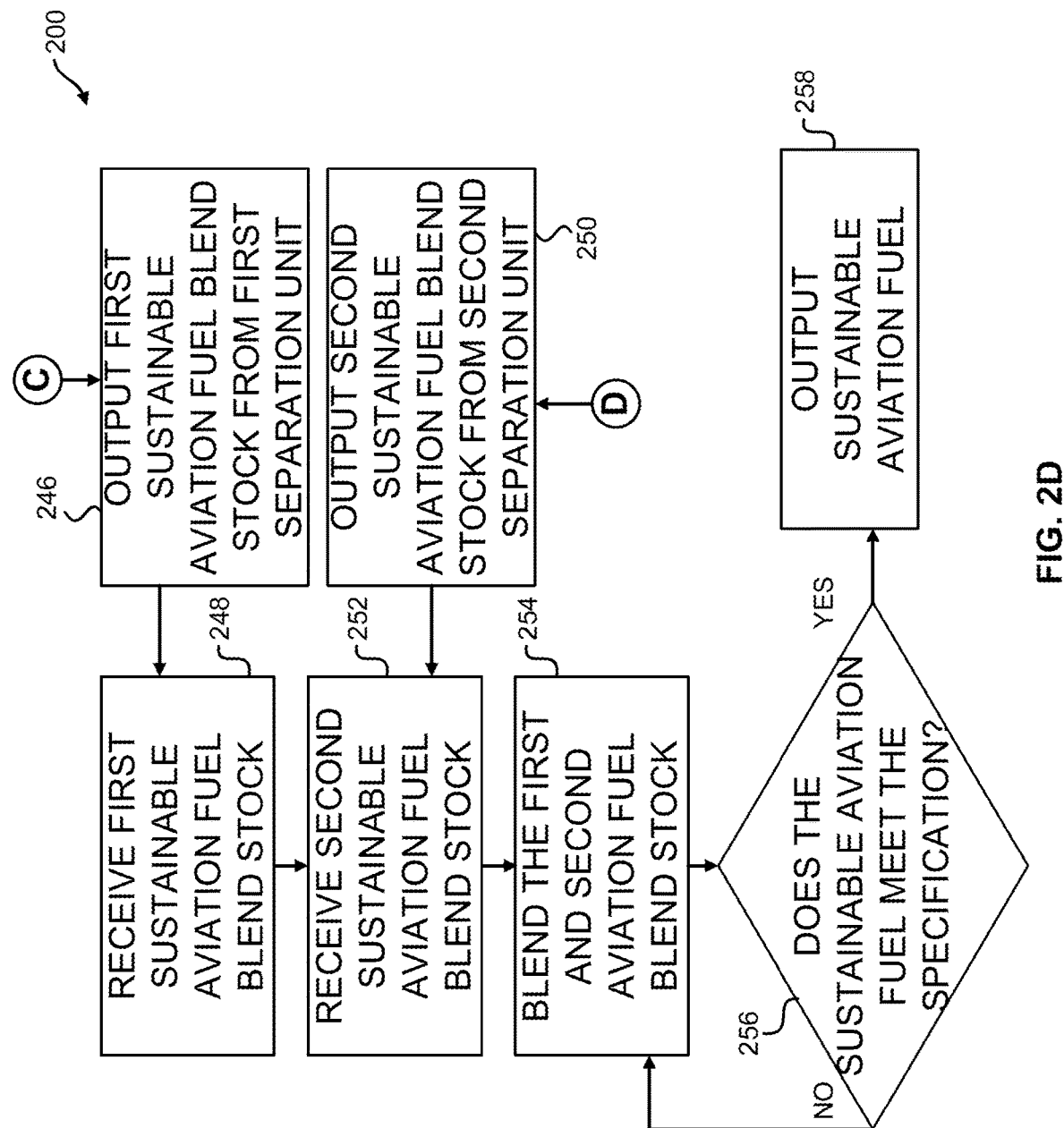
Figure 2F:
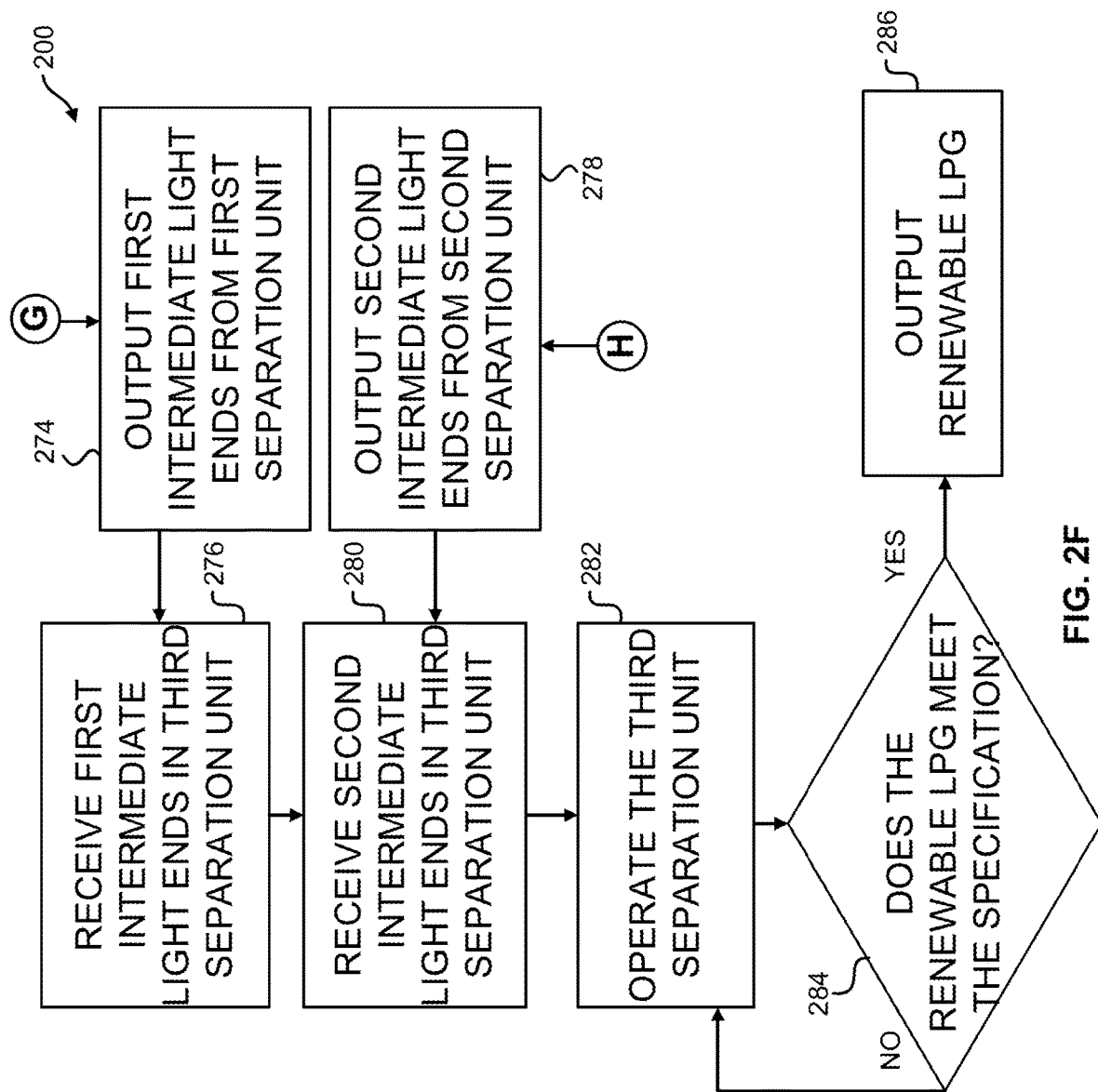

So that the manner in which the features and advantages of the embodiments of the systems and methods disclosed herein, as well as others, which will become apparent, may be understood in more detail, a more particular description of embodiments of systems and methods briefly summarized above may be had by reference to the following detailed description of embodiments thereof, in which one or more are further illustrated in the appended drawings, which form a part of this specification. It is to be noted, however, that the drawings illustrate only various embodiments of the embodiments of the systems and methods disclosed herein and are therefore not to be considered limiting of the scope of the systems and methods disclosed herein as it may include other effective embodiments as well.

Recently enacted low carbon fuel standards provide incentives for converting bio-feedstocks into refined products for use in transportation fuels, and technologies have been developed to produce such refined products. These refined products are transported to a traditional refinery or terminal to be blended into fossil-based fuels or otherwise upgraded. Such transportation and further upgrading may involve the use of high carbon intensity methods (e.g., long-haul trucks using fossil fuels, significant processing at the refinery, etc.). The renewable diesel facility, biodiesel facility, ethanol plant, and other renewable transportation fuel units are typically located at or in separate sites or locations apart from each other and traditional refineries/blend terminals. As such, products produced by each unit are transported for blending or further processing. For example, the diesel product formed by some renewable diesel units contain ringed components, have low cetane (e.g., a cetane number between about −30 to 10), and is dark in color. Such a diesel product cannot be blended into California Air Resources Board (CARE) diesel or ultra-low sulfur diesel (ULSD) diesel at appreciable volumes without further processing.

Applicants have recognized a need for systems and methods to provide renewable transportation fuels for internal combustion engines by converting renewable feedstocks into two or more intermediate hydrocarbon blend stocks and blending at least two of the two or more intermediate hydrocarbon blend stocks to produce the renewable transportation fuel. The renewable feedstocks may be produced at a refinery or facility via co-located, on-site units. Additionally, the renewable feedstocks may be converted using renewable utilities, such as renewable natural gas, renewable electricity (via wind, solar, or hydroelectric), etc. Moreover, the renewable natural gas may be used, e.g., in a steam reformer, to produce hydrogen for hydrotreating and/or hydrocracking operations. Thus, the co-location of at least a renewable diesel production unit, renewable naphtha/gasoline unit, and renewal natural gas fed steam reformer enables the production of one or more of a low carbon intensity, fully renewable liquefied petroleum gas (LPG), gasoline, jet, diesel, marine fuel, and other petrochemicals. Such products are non-petroleum-based fuels, which are substantially devoid of fossil fuel-based components. Additionally, one or more other biomass or renewable feedstock units, such as an ethanol plant, may be co-located for the production and blending of ethanol into the final transportation fuel. Further, renewable utilities, such as renewable natural gas, renewable electricity, etc., may be supplied to the process to further increase the sustainability of the produced transportation fuels. Since the renewable diesel production unit, the biodiesel production unit, the renewable naphtha/gasoline, renewable natural gas fed steam reformer, and other transportation fuel units (e.g., ethanol plant), all supplied by renewable utilities, may be co-located, the refinery or facility may be operated to produce a one hundred percent or near one hundred percent renewable biomass feedstock with a low carbon intensity, at least in relation to state of the art biofuel transportation and/or processing. Thus, the co-location of two or more of the above-described renewable fuel units can create or define a fully renewable, or near-fully renewable, bio-refinery that introduces efficiencies and/or margin enhancements in excess of what may be achieved if the units are located at separate facilities or are co-located at a petroleum-based refinery. Additionally, the co-location of one or more of the above-described renewable fuel units with a conventional crude oil refinery can create or define a near-fully renewable refinery that introduces efficiencies and/or margin enhancements in excess of what may be achieved if the units are located at separate facilities or at facilities apart from a conventional petroleum-based refinery.

The renewable diesel unit of a co-located refinery performs hydrodeoxygenation (HDO) and isomerization steps on biomass-based or biomass-derived feedstocks, including, but not limited to, vegetable oils, animal fats, used cooking oil, other lipids, or some combination thereof. Such HDO and isomerization steps produce renewable diesel, naphtha or a low-grade naphtha, liquefied petroleum gas (LPG), and other fuel gas products.

The renewable gasoline and/or other transportation fuel processes (e.g., such as the Virent BioForming® processes) of the co-located refinery convert sugars, such as glucose, and other aqueous carbohydrates into a renewable gasoline product (e.g., such as a Bioformate® product). Such renewable gasoline and/or other transportation fuel processes may include the three process steps of hydrogenation (HYD), HDO, and acid condensation (AC) that is then followed by a separations process to thereby separate out the renewable gasoline product and/or other renewable transportation fuel products (e.g., aviation, marine, jet, light ends, or other products). The renewable gasoline product and/or other renewable transportation fuel products can be processed using existing refining and petrochemical technologies into a range of hydrocarbon products, biofuel products, and key renewable chemicals, including aromatics, diesel, LPG, fuel gas, bio p-xylene and bio benzene. Thus, the renewable gasoline and/or other transportation fuel processes transform renewable plant sugars into the same range of hydrocarbon molecules (i.e., cut points) produced by refining petroleum.

Rather than having each unit in a separate location or facility, renewable diesel, biodiesel, renewable gasoline, and/or other transportation fuel units (e.g., ethanol plant, etc.) are co-located, allowing for the co-mingling of intermediate streams, the blending of products, and the shared use of hydrogen production, separations, utilities, and logistics infrastructure. Further, the renewable diesel unit, biodiesel unit, renewable gasoline and/or other transportation fuel units may be configured to be added as a kit or retrofit at an existing refinery, e.g., enabling use of existing equipment. In such examples, some units or equipment may be adapted or re-configured for use in such processes (e.g., configured to resist highly corrosive products, different temperature ranges, and/or other characteristics, as will be understood by a person skilled in the art).

As used herein, "carbon intensity" refers to the quantification of the direct and indirect release of greenhouse gases attributable to consumer and/or industrial activity. The carbon intensity or emission intensity was developed as a measure of the greenhouse gases emitted per unit of activity/production. With respect to transportation fuel, hydrogen production, other chemical production, and use of such products, the carbon intensity may be defined as the lifecycle greenhouse gases emitted per unit of energy. By assessing the lifecycle greenhouse gas emissions, all greenhouse gas emissions attributable to the fuel or hydrogen are accounted for during the entire lifecycle of the fuel or hydrogen from acquisition to processing to combustion. The carbon intensity for transportation fuels and hydrogen is often reported in units of grams of carbon dioxide equivalent per mega joule of energy. Because some greenhouse gases, such as methane, are considered to have a greater climatic effect than carbon dioxide, greenhouse gas emissions are reported in carbon dioxide equivalents.

FIG. 1 is a schematic diagram of a co-located refinery 172, according to one or more embodiments disclosed herein. The co-located refinery 172 may include various components, equipment, or units to produce various transportation fuels, particularly renewable transportation fuels. The co-located refinery 172 may utilize various, different feedstock to produce the transportation fuels. The various processes utilized within the co-located refinery 172 may be implemented by different units, e.g., a renewable diesel unit 120, a renewable gasoline or other transportation fuel unit 170, a blending unit 154, a hydrogen production unit 122, and/or other equipment or units, as will be described below.

As noted, the co-located refinery 172 may include a renewable diesel unit 120. The renewable diesel unit 120 may accept as feedstock fats and oils or other lipids 104. The fats and oils or other lipids 104 may include vegetable oils, animal fats, used cooking oil, other lipids, or some combination thereof. The fats and oils or other lipids 104 may be provided to the co-located refinery 172 via various transportation modes, such as rail, vehicle, marine vessel, and/or pipeline, and from various sources. One source may include a wet or dry mill 154, which may provide oil 110 to the co-located refinery 172, as will be described in further detail below.

The renewable diesel unit 120 may generate renewable diesel via hydrotreating or hydroprocessing of the fats and oils or other lipids 104. The renewable diesel unit 120 may perform hydrodeoxygenation and isomerization of the fats and oils or other lipids 104 or other biomass-based feedstock. Other biomass-based feedstock may include crop residues, wood, sawdust, and/or switchgrass. The renewable diesel unit 120 may utilize hydrogen 124 in the processes described herein, the hydrogen 124 provided from a hydrogen production unit 122. The renewable diesel unit 120 may produce one or more output streams. The one or more output streams may include low-grade naphtha 126, naphtha, renewable diesel 128, and/or sustainable aviation fuel 130. The renewable diesel unit 120 may connect to a separator 152. The one or more streams may feed into the separator 152. The naphtha or low-grade naphtha 126 may include a benzene content of less than about 0.5 volume percent and a research octane number (RON) of less than about 60.

As noted, the co-located refinery 172 may include a renewable gasoline or other transportation fuel unit 170. The renewable gasoline or other transportation fuel unit 170 may include various equipment or components. For example, the renewable gasoline or other transportation fuel unit 170 may include a HYD reactor 112, a HDO reactor 114, and/or an AC unit 116. The HYD reactor 112 may reduce or saturate organic compounds via a chemical reaction between hydrogen 124 (e.g., from the hydrogen production unit 122) and the feedstock (e.g., sugar 106 or sugar 108), with or without a catalyst. For example, the HYD reactor 112 may produce a HYD sugar. The HDO reactor 114 may remove oxygen from the product of the HYD reactor 112 via a hydrogenolysis process. Hydrogen 124 (e.g., from the hydrogen production unit 122) may be utilized in such a process. Further, since sugar is an oxygen-rich precursor, such a process hydrogenolysis process may be utilized. The product of the HDO reactor 114 may be a HDO, HYD sugar. The product of the HDO reactor 114 may be fed to an AC unit 116. The AC unit 116 may condense any acid gases within the product from the HDO reactor 114 and remove the resulting acidic condensate.

In an embodiment, the renewable gasoline or other transportation fuel unit 170 may include a separator 118. In another embodiment, the separator 118 may not be considered a part of the renewable gasoline or other transportation fuel unit 170, but rather a separate component or separate equipment. The separator 118 may separate different fluids and/or gases from the product of the AC unit 116. The separator 118 may separate such a product into marine fuel 136, aviation fuel 138, and/or gasoline blend feedstock 140. The aviation fuel 138 may include or contain synthesized kerosene (SK) and/or synthesized aromatic kerosene (SAK).

In an embodiment, sugar 106, 108 may be provided to the renewable gasoline or other transportation fuel unit 170. The sugar 106, 108 may be provided from a number of sources. For example, sugar 106 may be sourced from food waste, a refined sugar source (e.g., sugar cane, etc.), and/or sugar from other sources (e.g., corn, beets, grains, etc.).

In an embodiment, a wet or dry mill 154 may provide sugar 108, oil 110, and/or ethanol 132 to the co-located refinery 172. As illustrated, the wet or dry mill 154 may be located separately and at varying distances (e.g., nearby or at long distances). In another embodiment, the wet or dry mill 154 may be co-located at the co-located refinery 172. In an embodiment, a wet mill may include tanks to soak fermentable feedstock (e.g., corn) in a dilute aqueous sulfur dioxide solution. The softened fermentable feedstock (e.g., corn) may be processed to remove the germ. The germ may be processed to produce oil (e.g., corn oil) for various uses (e.g., renewable diesel production or animal feed). The remaining portion of the fermentable feedstock (e.g., after germ removal) is processed to produce feed and starch, as will be understood by those skilled in the art. The starch may further be processed into ethanol, e.g., in a co-located or off-site ethanol plant, as will be understood by those skilled in the art.

In an embodiment, a dry mill may include a mill to grind a fermentable feedstock to grist or meal of a particular granularity. A fermentable feedstock may include organic matter including starches and/or sugar (e.g., corn, barley, wheat, sugar cane, beets, etc.) from a variety of sources. The grist or meal may be transported for liquefaction and/or saccharification, where the meal or grist is combined with a liquid (e.g., water) and heated to a specified temperature to form a mash or mixture. An amount of and type of enzymes (such as amylase) may be utilized (if any are to be used) to aid in the production of sugars/saccharides from starches in the mash or mixture. Yeast may be added to the mash or mixture once it has been cooled to a specified temperature. The yeast may then enable fermentation of the sugars in the mash or mixture. The fermented mash or mixture may then be distilled thereby forming ethanol. By-products of the process described for the dry mill and wet mill may include additional sugar and/or oil, in addition to carbon dioxide (e.g., produced during fermentation). As such and as noted, the wet or dry mill 154 may provide sugar 108, oil 110, and/or ethanol 132 to the co-located refinery 172.

As noted above, several processes or units at the co-located refinery 172 may utilize hydrogen 124. Thus, the co-located refinery 172 may include a hydrogen production unit 122. The hydrogen production unit 122 may be a typical steam reformer and/or an electrolyzer. The input or feedstock for a steam reformer may include a renewable natural gas (RNG) 102, a typical fossil fuel based natural gas, or some combination thereof. The steam reformer may be a methane steam reformer. The steam reforming process may produce hydrogen and carbon dioxide, among other gases, as will be understood by a person skilled in the art. In a further embodiment, a portion of the renewable transportation fuel, particularly the renewable LPG 162, or any other intermediate product may be utilized in a burner or furnace associated with the hydrogen production unit 122.

In another embodiment, rather than or in addition to a steam reformer, an electrolyzer may be utilized to generate hydrogen. The feedstock for the electrolyzer may include varying types of water, such as gray water, treated gray water, salt water, fresh water, and/or other types of water, as will be understood by those skilled in the art. The energy or electricity utilized to produce the hydrogen in an electrolyzer may be provided via typical fossil-fuel based generators, wind turbines, solar arrays, geothermal power plants/facilities, RNG-fired turbines, and/or RNG-produced steam letdown.

The co-located refinery 172 may include one or more separators 118, 150, 152. The separator 118 associated with or included with the renewable gasoline or other transportation fuel unit 170 may output, as noted, a marine fuel 136, an aviation fuel 138, a gasoline blend stock 140, and/or light ends 148. The separator associated with or included with the renewable diesel unit 120 may output marine fuel 136, aviation fuel 142, low-grade naphtha 134, and/or light ends 146. The co-located refinery 172 may include another separator 150. The separator 150 may receive the light ends 146 from separator 152 and light ends 148 from separator 118. The separator 150 may output a renewable LPG 162. In an embodiment, the aviation fuel 142 may include or contain hydroprocessed esters and fatty acids-synthetic paraffinic kerosene (HEFA-SPK).

The co-located refinery 172 may include a blend unit 154. The blend unit 154 may include several blend sub-units 156, 158, 160. The blend sub-units 156, 158, 160 may be a tank or an in-line mixing system. In embodiments, the type of blend sub-unit may depend on the type of blend to be output or the input into the blend sub-unit. In an example, to produce a renewable gasoline 164, a low-grade naphtha 134, gasoline blend stock 140, and/or ethanol 132 may be blended in blend sub-unit 1 156. To produce a sustainable aviation fuel 166, an aviation fuel 142 and aviation fuel 138 may be blended in blend sub-unit 2 158. To produce a sustainable marine fuel 168, a marine fuel 136 and marine fuel 136 may be blended in blend sub-unit 3 160.

Several of the processes described above and herein may produce an amount of carbon dioxide and or other gases that may be deemed to be adverse to the environment. To further reduce carbon dioxide output or carbon intensity of a resulting product (e.g., renewable LPG 162, renewable gasoline 164, sustainable aviation fuel 166, and/or sustainable marine fuel 168), several carbon reduction processes may be utilized. For example, each process may utilize a heat exchanger network. The heat exchanger network may include one or more heat exchangers that are arranged to provide heat to process streams (e.g., process streams to be heated) by exchanging heat with other process streams to be cooled. Thus, rather than burning fuel or using electricity to provide heat to a process, waste heat may be utilized. In another example, any of the various processes described herein may utilize electricity generated from wind turbines, solar arrays, geothermal power plants/facilities, RNG-fired turbines, and/or RNG-produced steam letdown. In yet another example, any of the processes described herein that produce carbon dioxide may utilize carbon capture and sequestration methods or processes to further reduce carbon output or carbon intensity.

In an embodiment, the resulting product (e.g., renewable LPG 162, renewable gasoline 164, sustainable aviation fuel 166, and/or sustainable marine fuel 168) of the co-located refinery 172 may be a 100% renewable product. In yet another embodiment, the co-located refinery 172 may include other refining equipment or units to produce fossil fuel based products. The fossil fuel based products may be blended with the products from the renewable diesel unit 120 and/or the renewable gasoline or other transportation fuel unit 170, as well as ethanol 132, thus forming a transportation fuel that includes at least a portion or a substantial portion of renewable transportation fuel.

FIGS. 2A-2F are flow diagrams for providing or producing renewable transportation fuels according to an embodiment. The method 200 is detailed with reference to the co-located refinery 172 of FIG. 1. The actions of method 200 may also be completed or implemented within the controller 302. Specifically, method 200 may be included in one or more programs, protocols, or instructions loaded into the memory 306 of the controller 200 and executed on the processor 304 or one or more processors of the controller 200. The order in which the operations are described is not intended to be construed as a limitation, and any number of the described blocks may be combined in any order and/or in parallel to implement the methods.

At block 202, the co-located refinery 172 or a controller (e.g., controller 302) at the co-located refinery 172 may receive a type of fuel to blend and/or specification for the type of fuel. A specification for a type of fuel may be based on California Air Resources Board (CARE) diesel standards or ultra-low sulfur diesel (ULSD) diesel standards, among other fuel standards as will be understood by the person skilled in the art. Parameters included in the specification may include types of fuel to blend, amount or percentage of each fuel in the final blend, amount of sulfur allowable in the blend, a carbon intensity of the blend, cetane number, octane number, RON, motor octane number, and/or other fuel parameters. The specification may additionally include the final type of fuel, e.g., such as marine fuel, aviation fuel, diesel, gasoline, LPG, and/or other fuels as will be understood by a person skilled in the art.

At block 204, the sugar 106 for the process may be selected. The sugar 106 may include one or more different types of sugar 106 in one or more different forms (e.g., solid or liquid). The sugar 106 may be transported to the co-located refinery 172 upon selection. In other embodiments, the one or more types of sugar 106 may be at or proximate to the co-located refinery 172.

At block 206, the sugar 106 may be introduced to one or more reactors (e.g., at a renewable gasoline or other transportation fuel unit 170). The one or more reactors may include a HYD 112 reactor and an HDO reactor 114. An AC unit 116 may be included in the renewable gasoline or other transportation fuel unit 170, and the product of the a HYD 112 reactor and an HDO reactor 114 may pass through the AC unit 116.

At block 208, sugar 106 may be converted to an intermediate blend stock. Such a conversion may occur via operation of the one or more reactors. Such an operation may produce an intermediate blend stock. The resulting intermediate blend stock, at block 210, may be passed through a first separation unit (e.g., separator 118). The first separation unit may produce one or more different feedstock (e.g., a gasoline blend stock, aviation blend stock, marine blend stock, and/or light ends). The gasoline blend stock may be output from the separation unit to a first blend unit (e.g., blend unit 1 156).

At block 214, a lipid (e.g., fats and oils or lipids 104) may be selected, for example, by the controller 302 or the co-located refinery 172. The lipid may be selected based on a type of fuel to be produced. The lipid may include one or more of vegetable oils, animal fats, used cooking oil, other lipids, or some combination thereof.

At block 216, once the lipid is selected, the lipid may be introduced to the renewable diesel unit 120. At block 218, once the lipid is introduced to the renewable diesel unit 120, the renewable diesel unit 120 may be operated to produce one or more of diesel, naphtha or low-grade naphtha, sustainable aviation fuel blend stock, and/or sustainable marine fuel blend stock.

At block 220, the products of the renewable diesel unit 120 may be passed to a second separation unit (e.g., separator 152). The second separation unit may output various products, such as naphtha, aviation fuel, marine fuel, and/or light ends. At block 222, the naphtha may be output from the second separation unit and transported to the first blend unit (e.g., blend unit 1 156).

At block 224, the naphtha, gasoline blend stock, and/or an ethanol blend stock may be blended in the first blend unit according to the specification. In other words, the specified amounts of each product may be output to the first blend unit or each product may be blended to thereby form a final blend or product meeting the parameters of the specification.

At block 226, the resulting product may be sampled or measured to determine a composition of the blend. Such sampling or measurement may occur to determine whether the blend meets the specification (e.g., octane number, sulfur content, etc.). If the resulting blend does not meet the specification, additional products may be added to the blend, based on the type and value of the parameter that does not meet the specification. At block 228, if the blend meets the specification or parameters of the specification, a renewable gasoline may be output for use in an internal combustion engine.

At block 230, a carbohydrate feedstock or a fermentable feedstock may be introduced to an ethanol plant (e.g., wet or dry mill 154). In an embodiment, the ethanol plant may be included at the co-located refinery 172 or separate from the co-located refinery 172.

At block 232, the carbohydrate feedstock or a fermentable feedstock may be fermented. Other steps may be included in the ethanol production. At block 234, the fermented carbohydrate may be distilled to produce ethanol or a blend stock. At block 236, the blend stock may be sent to a third separation unit and, at block 238, ethanol may be output form the third separation unit. In another embodiment, after distillation, the ethanol may be sent directly to a first blend unit for blending, rather than to a separator.

At block 240, RNG 102 or another natural gas may be introduced to a reformer (e.g., hydrogen production unit 122). The reformer, at block 242, may be operated to produce hydrogen 124 from the RNG 102. At block 244, the hydrogen 124 may be sent to the renewable diesel unit 122. In an embodiment, other units at the co-located refinery may utilize the hydrogen (e.g., the HYD 112 and/or the HDO 114, among other units).

At block 246, the first separator may output an aviation fuel blend stock. The first aviation fuel blend stock may be output to or received by a second blend unit, at block 248. At block 250, the second separator may output a second aviation fuel blend stock. The second aviation fuel blend stock may be output to or received by the second blend unit, at block 252. Once the appropriate amount of each blend stock is received, the second blend unit may be operated to blend the first and second aviation fuel blend stock. The resulting blend may be sampled or analyzed to determine whether the blend meets the specification or specification parameters, at block 256. If the parameters are not met, the blend may be adjusted, by adding more of either of the blend stocks. If the blend does meet the specification, the blend may be output as a sustainable aviation fuel, at block 258.

At block 260, the first separator may output a marine fuel blend stock. The first marine fuel blend stock may be output to or received by a third blend unit, at block 260. At block 264, the second separator may output a renewable diesel. The renewable diesel, which may be considered ULSD, may be output to or received by the third blend unit, at block 266. Once the appropriate amount of each blend stock is received, the third blend unit may be operated to blend the first marine fuel blend stock and the renewable diesel. The resulting blend may be sampled or analyzed to determine whether the blend meets the specification, at block 270. If the parameters are not met, the blend may be adjusted, by adding more of either of the blend stocks. If the blend does meet the specification, the blend may be output as a sustainable aviation fuel, at block 272.

At block 274, the first separator may output first light ends. The first light ends may be output to or received by a third separator, at block 276. At block 278, the second separator may output second light ends. The second light ends may be output to or received by the third blend unit separator, at block 280. Once the appropriate amount of each light end is received, the third separator, at block 282, may be operated to produce a renewable LPG. The resulting renewable LPG may be sampled or analyzed to determine whether the renewable LPG meets the specification, at block 284. If the parameters are not met, the renewable LPG may be adjusted, by adding more of either of the light ends. If the renewable LPG does meet the specification, the renewable LPG may be output, at block 286.

Figure 3A:
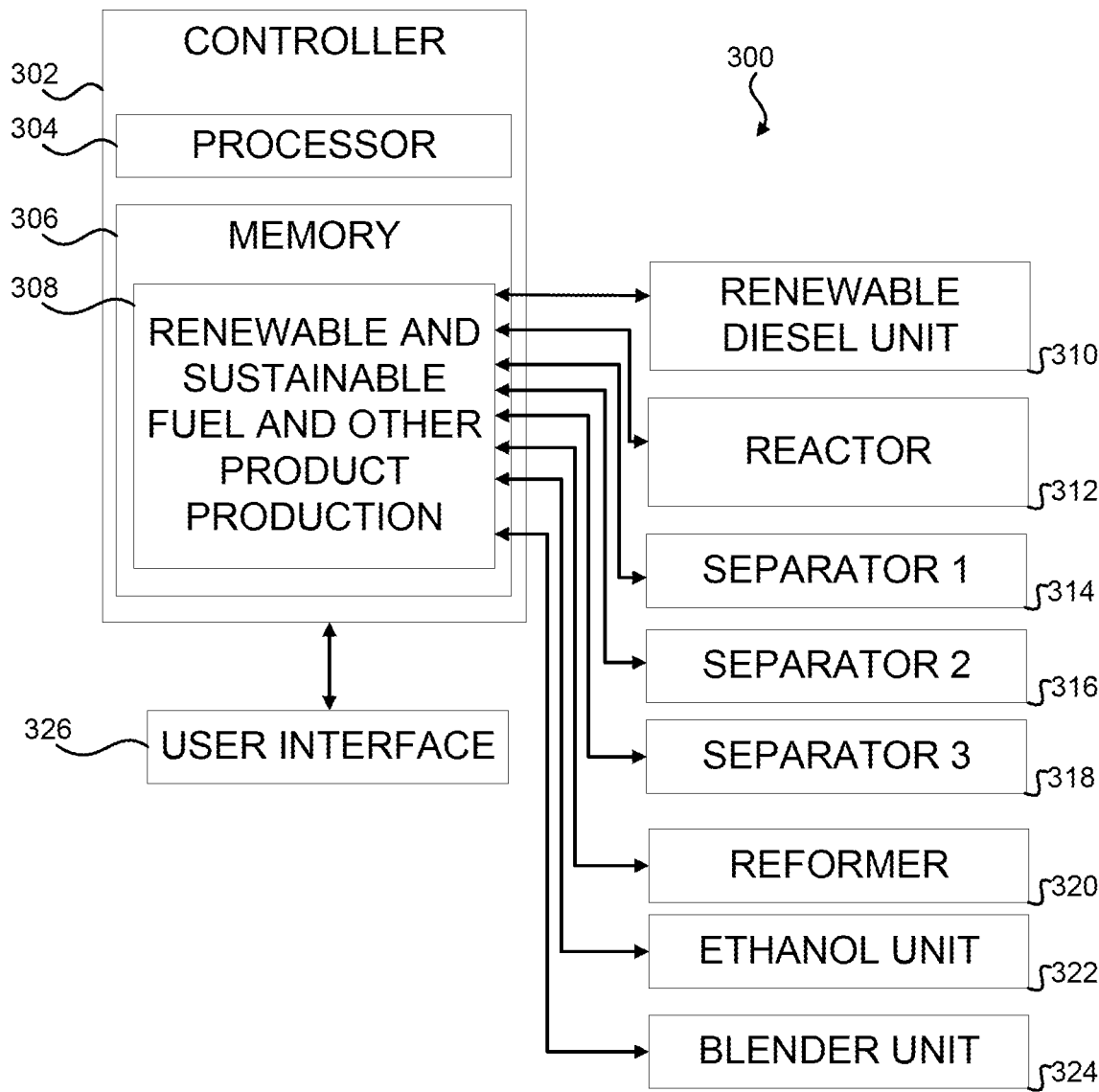
FIGS. 3A through 3B are schematic diagrams of one or more controllers to coordinate the production of the transportation fuel, according to one or more embodiments disclosed herein.
Figure 3B:
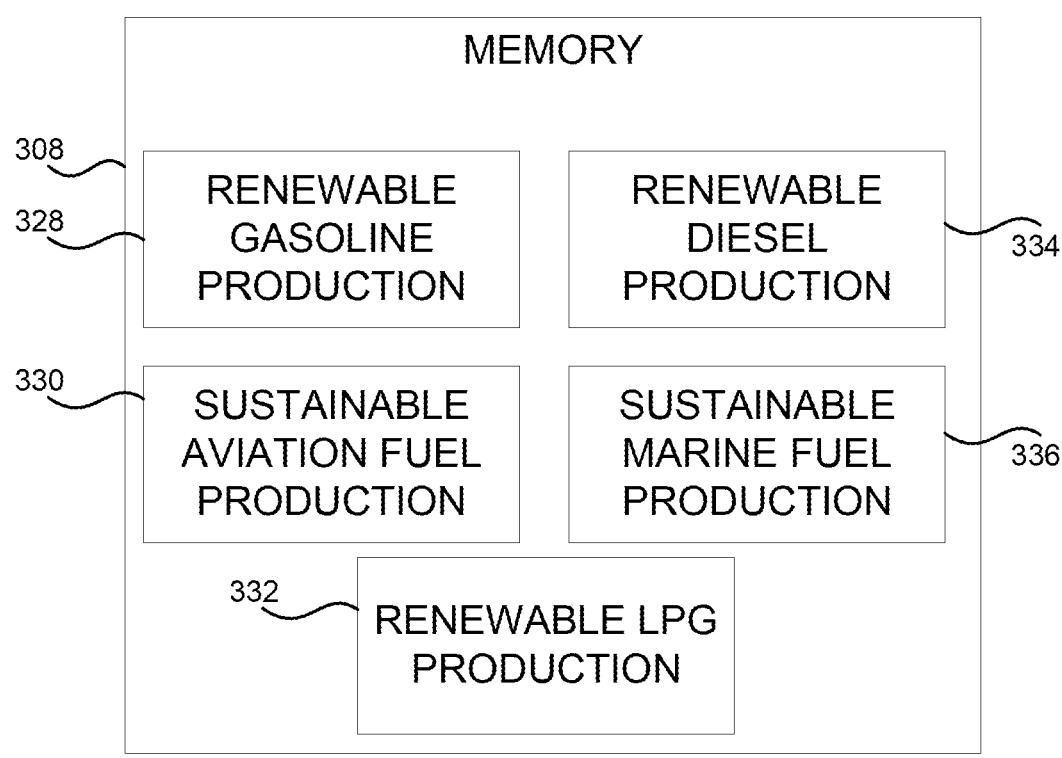

FIGS. 3A through 3B are simplified diagrams illustrating a control system 300 for managing the production of renewable transportation fuels, according to one or more embodiments disclosed herein. In an example, the control system 300 may include a controller 302 or one or more controllers. Further, the controller 302 may be in signal communication with various other controllers throughout or external to the co-located refinery. The controller 302 may be considered a supervisory controller. In another example, a supervisory controller may include the functionality of controller 302.

Each controller described above and herein may include a machine-readable storage medium (e.g., memory 306) and one or more processors (e.g., processor 304). As used herein, a "machine-readable storage medium" may be any electronic, magnetic, optical, or other physical storage apparatus to contain or store information such as executable instructions, data, and the like. For example, any machine-readable storage medium described herein may be any of random access memory (RAM), volatile memory, non-volatile memory, flash memory, a storage drive (e.g., hard drive), a solid state drive, any type of storage disc, and the like, or a combination thereof. The memory 306 may store or include instructions executable by the processor 304. As used herein, a "processor" may include, for example one processor or multiple processors included in a single device or distributed across multiple computing devices. The processor 304 may be at least one of a central processing unit (CPU), a semiconductor-based microprocessor, a graphics processing unit (GPU), a field-programmable gate array (FPGA) to retrieve and execute instructions, a real time processor (RTP), other electronic circuitry suitable for the retrieval and execution instructions stored on a machine-readable storage medium, or a combination thereof.

As used herein, "signal communication" refers to electric communication such as hard wiring two components together or wireless communication, as understood by those skilled in the art. For example, wireless communication may be Wi-Fi®, Bluetooth®, ZigBee, or forms of near field communications. In addition, signal communication may include one or more intermediate controllers or relays disposed between elements that are in signal communication with one another. In the drawings and specification, several embodiments of renewable transportation fuel compositions and methods of making such renewable transportation fuel compositions are disclosed. The controller 302 may include instructions 308 to produce renewable and sustainable fuel and other products. Instructions 308, as illustrated in FIG. 3B may include several sub-routines, sub-instructions, or instructions to produce a number of sustainable and/or renewable transportation fuels.

The controller may include instructions 328, to cause a co-located refinery to produce a renewable gasoline. In such an example, the controller 302 may determine what type of gasoline to produce and what to include in such a product based on a specification received, for example, from a user interface 326. In another example, the specification may be pre-loaded into the instructions or memory 306, prior to initiation of such a process. Once such a process is initiated the controller 302 may send signals to the renewable diesel unit 310, the reactor 312, separator 1 314, separator 2 316, a reformer 320, an ethanol plant/unit 322, and/or a blender unit 324. The signals may include operating parameters for each unit, such as temperatures, length of operating time, amount of incoming feedstock, amount of product to be produced, as well as other parameters. Other parameters may include cetane number, RON number, MON number, sulfur content, among other parameters relevant to the renewable gasoline as will be understood by a person skilled in the art. The controller 302 may monitor the process until the process is complete and ensure that the final renewable gasoline meets the specification and, if not, then adjusting the blend of the renewable gasoline.

The controller 302 may include instructions 334, to cause a co-located refinery to produce a renewable diesel. In such an example, the controller 302 may determine what type of diesel to produce and what to include in such a product based on a specification received, for example, from the user interface 326. In another example, the specification may be pre-loaded into the instructions, prior to initiation of such a process. Once such a process is initiated the controller 302 may send signals to the renewable diesel unit 310, the reactor 312, separator 1 314, separator 2 316, a reformer 320, an ethanol plant/unit 322, and/or a blender unit 324. The signals may include operating parameters for each unit, such as temperatures, length of operating time, amount of incoming feedstock, amount of product to be produced, as well as other parameters. Other parameters may include cetane number, RON number, MON number, sulfur content, among other parameters relevant to renewable diesel (e.g., such as paraffinic content) as will be understood by a person skilled in the art. The controller 302 may monitor the process until the process is complete and ensure that the final renewable diesel meets the specification and, if not, then adjusting the blend of the renewable diesel.

The controller may include instructions 330, to cause a co-located refinery to produce a sustainable aviation fuel. In such an example, the controller 302 may determine what type of aviation fuel to produce and what to include in such a product based on a specification received, for example, from the user interface 326. In another example, the specification may be pre-loaded into the instructions, prior to initiation of such a process. Once such a process is initiated the controller 302 may send signals to the renewable diesel unit 310, the reactor 312, separator 1 314, separator 2 316, a reformer 320, an ethanol plant/unit 322, and/or a blender unit 324. The signals may include operating parameters for each unit, such as temperatures, length of operating time, amount of incoming feedstock, amount of product to be produced, as well as other parameters. Other parameters may include cetane number, RON number, MON number, sulfur content, among other parameters relevant to sustainable aviation fuel as will be understood by a person skilled in the art. The controller 302 may monitor the process until the process is complete and ensure that the final sustainable aviation fuel meets the specification and, if not, then adjusting the blend of the sustainable aviation fuel.

The controller may include instructions 336, to cause a co-located refinery to produce a sustainable marine fuel. In such an example, the controller 302 may determine what type of marine fuel to produce and what to include in such a product based on a specification received, for example, from the user interface 326. In another example, the specification may be pre-loaded into the instructions, prior to initiation of such a process. Once such a process is initiated the controller 302 may send signals to the renewable diesel unit 310, the reactor 312, separator 1 314, separator 2 316, a reformer 320, an ethanol plant/unit 322, and/or a blender unit 324. The signals may include operating parameters for each unit, such as temperatures, length of operating time, amount of incoming feedstock, amount of product to be produced, as well as other parameters. Other parameters may include cetane number, RON number, MON number, sulfur content, among other parameters relevant to sustainable marine fuel as will be understood by a person skilled in the art. The controller 302 may monitor the process until the process is complete and ensure that the final sustainable marine fuel meets the specification and, if not, then adjusting the blend of the sustainable marine fuel.

The controller may include instructions 332, to cause a co-located refinery to produce a renewable LPG. In such an example, the controller 302 may determine what type of LPG to produce and what to include in such a product based on a specification received, for example, from the user interface 326. In another example, the specification may be pre-loaded into the instructions, prior to initiation of such a process. Once such a process is initiated the controller 302 may send signals to the renewable diesel unit 310, the reactor 312, separator 1 314, separator 2 316, separator 3 318, a reformer 320, an ethanol plant/unit 322, and/or a blender unit 324. The signals may include operating parameters for each unit, such as temperatures, length of operating time, amount of incoming feedstock, amount of product to be produced, as well as other parameters. Other parameters may include cetane number, RON number, MON number, sulfur content, among other parameters relevant to renewable LPG as will be understood by a person skilled in the art. The controller 302 may monitor the process until the process is complete and ensure that the final renewable LPG meets the specification and, if not, then adjusting the blend of the renewable LPG.

In another embodiment, various sensors and meters may be disposed through the system 300 or the co-located refinery 172. Such sensors and meters may be in signal communication with the controller 302 and may provide data or feedback to the controller 302 to determine various properties of each unit and/or product at various stages in the process. The sensors and meters may measure flow, density, chemical properties, temperature, pressure, and/or other properties, as will be understood by a person skilled in the art.

This is a continuation of U.S. Non-Provisional application Ser. No. 17/848,443, filed Jun. 24, 2022, titled "SYSTEMS AND METHODS OF CONVERTING RENEWABLE FEEDSTOCKS INTO INTERMEDIATE HYDROCARBON BLEND STOCKS AND TRANSPORTATION FUELS," which claims priority to and the benefit of U.S. Provisional Application No. 63/262,426, filed Oct. 12, 2021, titled "SYSTEMS AND METHODS OF CONVERTING RENEWABLE FEEDSTOCKS INTO INTERMEDIATE HYDROCARBON BLEND STOCKS AND TRANSPORTATION FUELS," the disclosures of which are incorporated herein.

Although specific terms are employed herein, the terms are used in a descriptive sense only and not for purposes of limitation. Embodiments of systems and methods have been described in considerable detail with specific reference to the illustrated embodiments. However, it will be apparent that various modifications and changes can be made within the spirit and scope of the embodiments of systems and methods as described in the foregoing specification, and such modifications and changes are to be considered equivalents and part of this disclosure.

What is claimed is:

1. A process to provide renewable transportation fuels, the process comprising:
   introducing sugar into one or more reactors;
   converting the sugar into an intermediate renewable hydrocarbon blend stock within the one or more reactors;
   passing the intermediate renewable hydrocarbon blend stock through a first separation unit to separate out at least an intermediate renewable gasoline blend stock;
   introducing one or more lipids into a renewable diesel unit;
   operating the renewable diesel unit to yield a renewable diesel product from the one or more lipids, the renewable diesel product including at least a low-grade naphtha and a renewable diesel;
   passing the renewable diesel product through a second separation unit to separate out at least the renewable diesel and the low-grade naphtha, the low-grade naphtha having a benzene content less than about 0.5 volume percent and a research octane number of less than about 60;
   blending the low-grade naphtha and the intermediate renewable gasoline blend stock so that a resulting blend defines a finished renewable gasoline; and
   outputting the finished renewable gasoline.

2. The process of claim 1, further comprising:
   prior to introducing the sugar to one or more reactors, selecting the sugar from a sugar source; and prior to introducing the one or more lipids into the renewable diesel unit, selecting the one or more lipids from a lipid source.

3. The process of claim 2, wherein the sugar source comprises sugar processed in a wet or dry mill.

4. The process of claim 2, wherein the one or more lipids comprises one or more of vegetable oils, animal fats, or used cooking oil.

5. The process of claim 1, further comprising:
   introducing a carbohydrate feedstock to an ethanol plant;
   operating an ethanol fermentation and distillation process in the ethanol plant to convert the carbohydrate feedstock into at least an ethanol product;
   separating an ethanol blend stock from the ethanol product in an ethanol separator; and
   blending the ethanol blend stock with the low-grade naphtha and the intermediate renewable gasoline blend stock so that the resulting blend defines the finished renewable gasoline.

6. The process of claim 1, further comprising:
   introducing renewable natural gas as a reformer unit feedstock to a reformer unit;
   producing at least hydrogen gas through conversion of the renewable natural gas in the reformer unit; and
   introducing at least a portion of the hydrogen gas into at least one of the one or more reactors to hydrogenate the sugar or dehydrodeoxygenate the hydrogenated sugar.

7. The process of claim 1, further comprising:
   introducing renewable natural gas as a reformer unit feedstock to a reformer unit;
   producing at least hydrogen gas by conversion of the renewable natural gas in the reformer unit; and
   introducing at least a portion of the hydrogen gas into the renewable diesel unit to produce the renewable diesel and the low-grade naphtha.

8. The process of claim 1, wherein the intermediate renewable hydrocarbon blend stock further includes a first sustainable aviation fuel blend stock that contains synthesized kerosene (SK) or synthesized aromatic kerosene (SAK), and wherein the renewable diesel product further includes a second sustainable aviation fuel blend stock that contains hydroprocessed esters and fatty acids-synthetic paraffinic kerosene (HEFA-SPK).

9. The process of claim 8, further comprising:
   separating the first sustainable aviation fuel blend stock from the intermediate renewable hydrocarbon blend stock in the first separation unit;
   separating the second sustainable aviation fuel blend stock from the renewable diesel unit in the second separation unit; and
   blending the first sustainable aviation fuel blend stock and the second sustainable aviation fuel blend stock into a renewable sustainable aviation fuel.

10. The process of claim 1, wherein the intermediate renewable hydrocarbon blend stock further includes a precursor marine fuel blend stock.

11. The process of claim 10, further comprising:
    separating the precursor marine fuel blend stock from the intermediate renewable hydrocarbon blend stock in the first separation unit; and
    blending an amount of the renewable diesel with the precursor marine fuel blend stock to define a renewable marine fuel.

12. The process of claim 1, wherein the finished renewable gasoline is outputted as a non-petroleum-based fuel.

13. The process of claim 1, wherein the finished renewable gasoline is substantially devoid of any fossil fuel-derived components, and wherein the converting of the sugar comprises a conversion through (a) hydrogenation of the sugar, (b) hydrodeoxygenation of the hydrogenated sugar, and (c) acid condensation of the hydrodeoxygenated, hydrogenated sugar.

14. A process to provide renewable transportation fuels, the process comprising:
- introducing sugar into one or more reactors;
- converting the sugar into an intermediate renewable hydrocarbon blend stock within the one or more reactors;
- passing the intermediate renewable hydrocarbon blend stock through a first separation unit to separate out at least a first sustainable aviation fuel blend stock that contains synthesized kerosene (SK) or synthesized aromatic kerosene (SAK);
- introducing one or more lipids into a renewable diesel unit;
- operating the renewable diesel unit to yield a renewable diesel product from the one or more lipids;
- passing the renewable diesel product through a second separation unit to separate out at least a second sustainable aviation fuel blend stock that has at least one of hydroprocessed esters and fatty acids-synthetic paraffinic kerosene (HEFA-SPK);
- receiving the first sustainable aviation fuel blend stock from the first separation unit;
- receiving the second sustainable aviation fuel blend stock from the second separation unit;
- blending at least the first sustainable aviation fuel blend stock and the second sustainable aviation fuel blend stock so that a resulting blend defines a sustainable aviation fuel; and
- outputting the sustainable aviation fuel.

15. The process of claim 14, further comprising:
- prior to introducing the sugar to one or more reactors, selecting the sugar from a sugar source; and
- prior to introducing the one or more lipids into the renewable diesel unit, selecting the one or more lipids from a lipid source, and wherein the converting of the sugar comprises a conversion through (a) hydrogenation of the sugar, (b) hydrodeoxygenation of the hydrogenated sugar, and (c) acid condensation of the hydrodeoxygenated, hydrogenated sugar.

16. A process to provide renewable transportation fuels, the process comprising:
- introducing sugar into one or more reactors;
- converting the sugar into an intermediate renewable hydrocarbon blend stock;
- passing the intermediate renewable hydrocarbon blend stock through a first separation unit to separate out at least a sustainable marine fuel blend stock;
- introducing one or more lipids into a renewable diesel unit;
- operating the renewable diesel unit to yield a renewable diesel product from the one or more lipids;
- passing the renewable diesel product through a second separation unit to separate out at least a renewable diesel;
- receiving the sustainable marine fuel blend stock from the first separation unit;
- receiving the renewable diesel from the second separation unit;
- blending at least the sustainable marine fuel blend stock and the renewable diesel so that the resulting blend defines a sustainable marine fuel; and
- outputting the sustainable marine fuel.

17. The process of claim 16, further comprising:
- prior to introducing the sugar to one or more reactors, selecting the sugar from a sugar source; and
- prior to introducing the one or more lipids into the renewable diesel unit, selecting the one or more lipids from a lipid source, and wherein the converting of the sugar comprises a conversion through (a) hydrogenation of the sugar, (b) hydrodeoxygenation of the hydrogenated sugar, and (c) acid condensation of the hydrodeoxygenated, hydrogenated sugar.

18. A system to provide renewable transportation fuels, the system comprising:
- a source of sugar;
- at least one reactor, having an inlet to receive the sugar from the source of sugar and an outlet, configured to hydrogenate the sugar, hydrodeoxygenate the hydrogenated sugar, and facilitate acid condensation of the hydrodeoxygenated, hydrogenated sugar to produce an intermediate renewable hydrocarbon blend stock;
- a first separation unit connected to and in fluid communication with the outlet of the at least one reactor, the first separation unit operable to separate the intermediate renewable hydrocarbon blend stock into at least an intermediate renewable gasoline blend stock;
- a source of lipids;
- a renewable diesel unit having an inlet to receive one or more lipids from the source of lipids and an outlet, the renewable diesel unit configured to yield a renewable diesel product from the one or more lipids;
- a second separation unit connected to and in fluid communication with the outlet of the renewable diesel unit, the second separation unit operable to separate the renewable diesel product into at least a renewable diesel blend stock and a low-grade naphtha, the low-grade naphtha having a benzene content less than about 0.5 volume percent and a research octane number of less than about 60; and
- a blending unit that receives and blends together at least the intermediate renewable gasoline blend stock from the first separation unit and the low-grade naphtha from the second separation unit.

19. The system of claim 18, further comprising:
- a source of carbohydrate feedstock;
- an ethanol production plant with an inlet that receives the carbohydrate feedstock from the source of carbohydrate feedstock, the ethanol production plant operable to convert the carbohydrate feedstock into an ethanol blend stock that leaves the ethanol production plant through an outlet thereof; and
- a flow line between the outlet of the ethanol production plant and the blending unit to pass the ethanol blend stock to the blending unit for blending with the intermediate renewable gasoline blend stock and the low-grade naphtha.

20. The system of claim 18, further comprising:
- a source of renewable natural gas;
- a hydrogen production unit with an inlet that receives the renewable natural gas from the source of renewable natural gas, the hydrogen production unit operable to convert the renewable natural gas into a hydrogen gas that leaves the hydrogen production unit through one or more outlets thereof;
- a first flow line between the one or more outlets of the hydrogen production unit and the at least one reactor to provide a first portion of the hydrogen gas thereto; and
- a second flow line between the one or more outlets of the hydrogen production unit and the renewable diesel unit to provide a second portion of the hydrogen gas thereto.

* * * * *